(12) United States Patent
Citriniti et al.

(10) Patent No.: US 9,239,296 B2
(45) Date of Patent: Jan. 19, 2016

(54) SKINNING OF CERAMIC HONEYCOMB BODIES

(71) Applicant: Corning Incorporated, Corning, NY (US)

(72) Inventors: Joseph Henry Citriniti, Corning, NY (US); Parasuram Padmanabhan Harihara, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 31 days.

(21) Appl. No.: 14/217,848

(22) Filed: Mar. 18, 2014

(65) Prior Publication Data

US 2015/0268174 A1 Sep. 24, 2015

(51) Int. Cl.
*G01N 21/00* (2006.01)
*G01N 21/89* (2006.01)
*G01N 21/95* (2006.01)
(Continued)

(52) U.S. Cl.
CPC ........ *G01N 21/8914* (2013.01); *B28B 17/0072* (2013.01); *B28B 19/0038* (2013.01); *G01N 21/95* (2013.01); *G01N 21/952* (2013.01); *G01N 2201/06113* (2013.01); *G01N 2201/103* (2013.01)

(58) Field of Classification Search
CPC ....... B65G 47/00; G01N 21/00; G01N 29/00; G01B 11/00; H01L 22/00; F01N 11/00; F01N 3/00
USPC ........................................... 356/237.2–237.6
See application file for complete search history.

(56) References Cited

U.S. PATENT DOCUMENTS 4,203,673 A 5/1980 Buckson ........................ 356/446
4,338,028 A * 7/1982 Tailleur et al. ............. 356/239.4
(Continued)

FOREIGN PATENT DOCUMENTS

CN 101871895 10/2010
CN 202548069 11/2012
(Continued)

OTHER PUBLICATIONS

Patent Cooperation Treaty International Notification of Transmital of the International Search Report and The Written Opinion of the International Searching Authority, international application No. PCT/US2015/021131: mailing date Jul. 24, 2015, 13 pages.

*Primary Examiner* — Tarifur Chowdhury
*Assistant Examiner* — Isiaka Akanbi
(74) *Attorney, Agent, or Firm* — Charles A. Greene

(57) ABSTRACT

An in situ inspection system and method to inspect a honeycomb body skin in a skinning system. The inspection system includes a line illuminator to generate a line illumination on the skin perpendicular to an axial direction of the honeycomb body travel, and a detector to detect the line illumination scattered from the skin and generate a signal based on the detected line illumination. A controller is configured to receive the signal generated by the detector, compare the received signal to a previously stored defect free signal in real-time, and control at least one skinning process parameter based on the comparison. The method includes in situ inspecting the skin and controlling at least one skinning process parameter based on the inspection. In the method, the in situ inspection includes illuminating a line of the skin perpendicular to the axial direction and detecting the illuminated line scattered from the skin.

22 Claims, 6 Drawing Sheets

(51) Int. Cl.
  *B28B 17/00* (2006.01)
  *B28B 19/00* (2006.01)
  *G01N 21/952* (2006.01)

(56) References Cited

U.S. PATENT DOCUMENTS

| | | | |
|---|---|---|---|
| 5,691,811 A * | 11/1997 | Kihira | 356/239.1 |
| 5,966,213 A | 10/1999 | Shimosaka et al. | 356/376 |
| 6,045,898 A * | 4/2000 | Kishi | C08G 59/18 |
| | | | 428/292.1 |
| 6,061,126 A | 5/2000 | Yoshimura et al. | |
| 6,122,045 A | 9/2000 | Pike et al. | 356/237.1 |
| 6,429,157 B1 * | 8/2002 | Kishi | B29C 70/025 |
| | | | 428/116 |
| 7,239,588 B2 | 7/2007 | Gotoh et al. | 369/53.2 |
| 7,602,487 B2 | 10/2009 | Fukami et al. | 356/241.1 |
| 7,627,163 B2 | 12/2009 | Chang et al. | 382/141 |
| 2002/0100994 A1 | 8/2002 | Sander | |
| 2007/0091309 A1 * | 4/2007 | Kondo | 356/364 |
| 2007/0132988 A1 * | 6/2007 | Gargano et al. | 356/237.6 |
| 2009/0010523 A1 * | 1/2009 | Komaki | G01N 21/952 |
| | | | 382/141 |
| 2010/0045975 A1 * | 2/2010 | Zoeller, III | 356/239.2 |
| 2011/0052039 A1 | 3/2011 | Urabe et al. | |
| 2011/0116704 A1 * | 5/2011 | Zoeller, III | G01N 21/95692 |
| | | | 382/141 |
| 2011/0128370 A1 * | 6/2011 | Booth | G01N 21/95692 |
| | | | 348/125 |
| 2011/0141461 A1 | 6/2011 | Matsui et al. | 356/237.2 |
| 2011/0278753 A1 | 11/2011 | Breuer et al. | 264/40.1 |
| 2011/0298916 A1 | 12/2011 | Arden | 348/86 |

FOREIGN PATENT DOCUMENTS

| | | |
|---|---|---|
| EP | 0701116 | 3/1996 |
| EP | 1241465 | 9/2002 |
| EP | 2006666 A2 | 12/2008 |
| JP | 59071644 A | 4/1984 |
| JP | 59071844 A | 4/1984 |
| JP | 8285780 A | 4/1995 |
| JP | 11258169 | 9/1999 |
| WO | 9964845 | 12/1999 |
| WO | 2004057317 | 7/2004 |
| WO | 2009058247 | 5/2009 |

* cited by examiner

SKINNING OF CERAMIC HONEYCOMB BODIES

BACKGROUND

1. Field

Exemplary embodiments of the present disclosure relate to skinning of honeycomb bodies and, more particularly, to inspection of skinned honeycomb bodies and control of skinning honeycomb bodies.

2. Discussion of the Background

After-treatment of exhaust gas from internal combustion engines may use catalysts supported on high-surface area substrates and, in the case of diesel engines and some gasoline direct injection engines, a catalyzed filter for the removal of carbon soot particles. Filters and catalyst supports in these applications may be refractory, thermal shock resistant, stable under a range of $pO_2$ conditions, non-reactive with the catalyst system, and offer low resistance to exhaust gas flow. Porous ceramic flow-through honeycomb substrates and wall-flow honeycomb filters (generically referred to herein as honeycomb bodies) may be used in these applications.

Particulate filters and substrates may be difficult to manufacture to external dimensional requirements set by original equipment manufacturers (OEMs) and the supply chain due to drying and firing shrinkage during manufacturing. Consequently, ceramic cement may be used to form an exterior skin of a honeycomb body which has been machined or "contoured" to a desired dimension. As used herein, the term "honeycomb body" includes single honeycomb monoliths and honeycomb bodies formed by multiple honeycomb segments that are secured together, such as by using a ceramic cement to form a monolith. Ceramic cement may be mixed and applied to a fired, contoured or segmented honeycomb body and the wet skin allowed to dry. The act or process of applying ceramic cement to the exterior of the honeycomb body is referred to herein as "skinning" the honeycomb body. A honeycomb body having skin disposed thereon is referred to herein as a "skinned" honeycomb body.

Once the wet skin on the honeycomb body has dried an inspection of the skin can be conducted requiring labor, cost, and time. When a defect is found it may be too late to correct a skinning process that caused the defect in sequential parts skinned in the same production run. The defects may be corrected requiring additional labor, time, and cost, or the production run may have to be scrapped if the defects are not repairable causing lost production and manufacturing inefficiencies.

The above information disclosed in this Background section is only for enhancement of understanding of the background of the disclosure and therefore it may contain information that does not form any part of the prior art nor what the prior art may suggest to a person of ordinary skill in the art.

SUMMARY

Exemplary embodiments of the present disclosure provide a system to manufacture skinned honeycomb bodies.

Exemplary embodiments of the present disclosure also provide a method of manufacturing skinned honeycomb bodies.

Additional features of the disclosure will be set forth in the description which follows, and in part will be apparent from the description, or may be learned by practice of the disclosure.

An exemplary embodiment discloses an in situ inspection system to inspect a honeycomb body skin in a honeycomb body skinning system for at least one defect. The inspection system includes a part conveying unit that moves a honeycomb body comprising the skin disposed thereon in an axial direction, an inspection unit, and a controller. The inspection unit includes a line illuminator configured to generate a line illumination on the skin perpendicular to the axial direction, and a detector configured to detect the line illumination scattered from the skin and generate a signal based on the detected line illumination. The controller is configured to receive the signal generated by the detector, compare the received signal to a previously stored defect free signal in real-time, and control at least one skinning process parameter based on the comparison.

An exemplary embodiment also discloses a method of manufacturing skinned honeycomb bodies. The method includes conveying a honeycomb body comprising a skin disposed thereon in an axial direction, in situ inspecting the skin, comparing a signal to a previously stored defect free signal in real-time, and controlling at least one skinning process parameter based on the comparing. In the method, the in situ inspecting the skin includes illuminating a line of the skin perpendicular to the axial direction, detecting the illuminated line scattered from the skin, and generating the signal based on the detecting.

It is to be understood that both the foregoing general description and the following detailed description are exemplary and explanatory and are intended to provide further explanation of the disclosure.

BRIEF DESCRIPTION OF THE FIGURES

The accompanying drawings, which are included to provide a further understanding of the disclosure and are incorporated in and constitute a part of this specification, illustrate exemplary embodiments of the disclosure, and together with the description serve to explain the principles of the disclosure.

DETAILED DESCRIPTION

Figure 1:
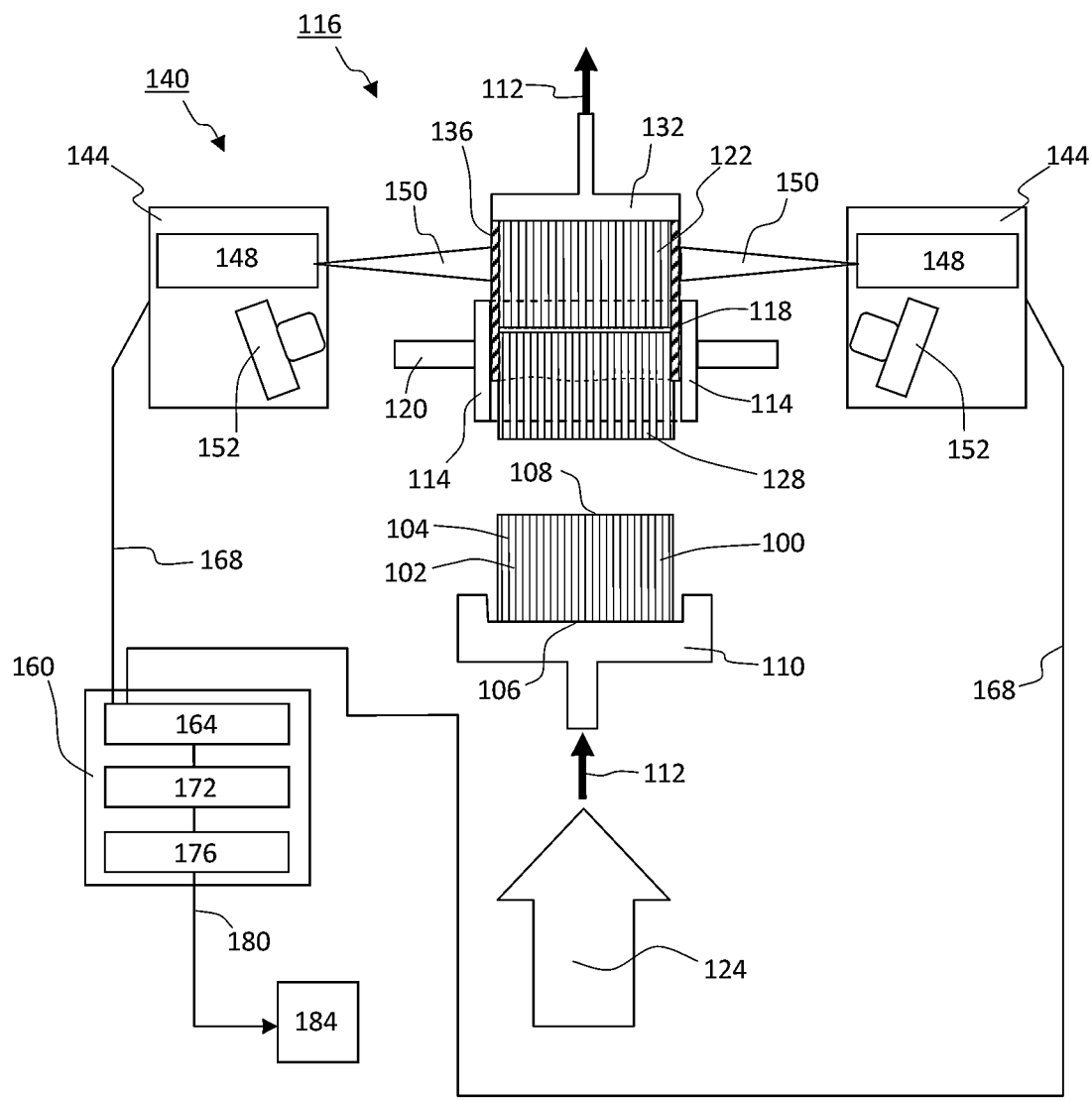
FIG. 1 shows a schematic of a system to manufacture skinned honeycomb bodies according to exemplary embodiments of the disclosure.

The disclosure is described more fully hereinafter with reference to the accompanying drawings, in which exemplary embodiments of the disclosure are shown. This disclosure may, however, be embodied in many different forms and should not be construed as limited to the exemplary embodiments set forth herein. Rather, these embodiments are provided so that this disclosure is thorough, and will fully convey the scope of the disclosure to those skilled in the art. In the drawings, the size and relative sizes of layers and regions may be exaggerated for clarity.

It will be understood that when an element or layer is referred to as being "on", "connected to", or "adjacent to" another element or layer, it can be directly on, directly connected to, or directly adjacent to the other element or layer, or intervening elements or layers may be present. In contrast, when an element or layer is referred to as being "directly on", "directly connected to", or "directly adjacent to" another element or layer, there are no intervening elements or layers present. Like reference numerals in the drawings denote like elements. It will be understood that for the purposes of this disclosure, "at least one of X, Y, and Z" can be construed as X only, Y only, Z only, or any combination of two or more items X, Y, and Z (e.g., XYZ, XYY, YZ, ZZ).

In these exemplary embodiments, the disclosed article, and the disclosed method of making the article provide one or more advantageous features or aspects, including for example as discussed below. Features or aspects recited in any of the claims are generally applicable to all facets of the disclosure. Any recited single or multiple feature or aspect in any one claim can be combined or permuted with any other recited feature or aspect in any other claim or claims.

While terms such as, top, bottom, side, upper, lower, vertical, and horizontal are used, the disclosure is not so limited to these exemplary embodiments. Instead, spatially relative terms, such as "top", "bottom", "horizontal", "vertical", "side", "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, employed in describing the embodiments of the disclosure, refers to variation in the numerical quantity that can occur, for example: through typical measuring and handling procedures used for preparing materials, compositions, composites, concentrates, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "RT" for room temperature, "nm" for nanometers, and like abbreviations).

Specific values disclosed for components, ingredients, additives, times, temperatures, pressures, and like aspects, and ranges thereof, are for illustration only; they do not exclude other defined values or other values within defined ranges. The apparatus, and methods of the disclosure can include any value or any combination of the values, specific values, and more specific values described herein.

As used herein, a green material is an unfired material comprising a mixture of inorganic and/or organic materials. The green material may include various inorganic filler materials, inorganic and/or organic binder materials, and liquid vehicle. The green material may be referred to herein as "wet" prior to drying. The green material may be dried to remove fluid content (e.g. water). Drying is often accomplished by allowing a part to sit exposed to the ambient atmosphere overnight, however, hot air, forced air, microwave, radio frequency (RF) or infrared radiation (IR) may be used to augment drying. The drying may be accomplished in humidity controlled air. Green material may include cold-set cements. The dried green material may be fired to form a porous or non-porous ceramic article.

As used herein, a "super addition" refers to a weight percent of a component, such as, for example, an organic binder, liquid vehicle, additive or pore former, based upon and relative to 100 weight percent of the inorganic components of the mixture.

Substrate and filter articles are used in gasoline and diesel, light duty and heavy duty vehicles for after treatment emission control, and which control satisfies environmental regulations. One of the steps in the production of these substrates and filters is the application of a cement-based skin or outer wall on the outer peripheral axial surface of the substrates and filters.

The skin on a part, such as a porous ceramic filter article, is the interface between the part and the surroundings. The skin serves several functions, for example, the skin adds to the aesthetics of the part and is valued by customers as an indicator of quality, protects the part's functional filter portion from structural degradation such as chipping damage, and other hazards surrounding the part, in manufacture and use, such as in handling and transport of the part, and adds to the isostatic strength of the part, which is a significant performance metric for modern parts.

FIG. 1 is a schematic diagram of an axial skinning system having an inline skin quality inspection and control unit according to exemplary embodiments of the disclosure.

FIG. 1 shows a honeycomb structure 100 to be skinned. The honeycomb structure 100 includes a plurality of intersecting walls 102 that form mutually adjoining cell channels 104 extending axially between opposing end faces 106, 108. The honeycomb structure 100 may be formed of a single monolith or formed of segments cemented together to form a monolith. The honeycomb structure 100 or part can optionally be first contoured or shaped, and then placed on a part handling unit 110. For ease of description, the received porous ceramic, such as honeycomb structure 100, will be referred to as an un-skinned part. The ceramic part received 100 may be un-skinned, contoured, include a base skin to be over-skinned, and the like. Contoured refers to a part shaped to particular dimensions and tolerances, for example, by grinding, machining, core drilling, cutting, or the like.

The un-skinned part 100 cell density can be between about 100 and 900 cells per square inch (cpsi). Typical cell wall thicknesses can range from about 0.025 mm to about 1.5 mm (about 1 to 60 mil). For example, honeycomb structure 100 geometries may be 400 cpsi with a wall thickness of about 8 mil (400/8) or with a wall thickness of about 6 mil (400/6). Other geometries include, for example, 100/17, 200/12, 200/19, 270/19, 600/4, 400/4, 600/3, and 900/2. As used herein, honeycomb is intended to include a generally honeycomb structure but is not strictly limited to a square structure. For example, hexagonal, octagonal, triangular, rectangular or any other suitable cell shape may be used. Also, while the cross section of the cellular un-skinned part 100 is depicted as circular, it is not so limited, for example, the cross section can be elliptical, square, rectangular, or other desired shape.

The part handling unit 110 can move the un-skinned part 100 in the axial direction as indicated by arrow 112 into a tube (unipipe) or skinning chamber 114 having a diameter that is slightly larger than the part. Unipipe 114 refers to a central structure of an axial skinning apparatus 116 that is adapted to receive a porous ceramic, such as the honeycomb structure 100 and further adapted to receive flowable cement 118 from a cement source (not shown) through a manifold 120 and to deliver the cement 118 to the surface of the ceramic part within the unipipe 112 to produce the skinned part 122. The skinning direction is indicated by arrow 124.

Honeycomb structure 128 is shown partially skinned in FIG. 1 as it moves through the unipipe 114. Part handling unit 110 and part lifting unit 132 can provide a motive force to move the part 128 through the unipipe 112. Honeycomb body 122 is shown exiting the unipipe 114 comprising a uniform layer of cement 118 forming a wet skin 136 on the outer periphery of the honeycomb structure. For ease of description, the skinned porous ceramic, such as honeycomb body 122, will be referred to as a part.

Skin material disclosed herein can include those that set at a temperature of less than 200° C., such as a temperature of less than 100° C., and further such as a temperature of less than 50° C., including cement material that can be used in skinning processes employing "cold set" skins. In cold set skinning, only drying of the skinning mixture is required to form a seal of the channel walls of the honeycombs. When a cold set skinning process is employed, heating of the skinned honeycombs to temperatures in the 35-110° C. range can be useful to accelerate drying. In some cold set skinning processes, it is anticipated that final skin consolidation, including the removal of residual temporary binder bi-products such as the sheet 130 and strengthening of the seals, can occur in the course of subsequent processing steps (e.g., in the course of catalyzation or canning) or during first use (e.g., in an exhaust system).

For example, exemplary compositions in which cold set skinning may be employed include those comprising a refractory filler that comprises at least one inorganic powder, such as at least one of aluminum titanate, cordierite, fused silica, mullite, and alumina, the inorganic powder having a bimodal or mono sized median particle size ($D_{50}$) of from 15 to 50 microns, such as from 30 to 40 microns for mono sized and additionally a median particle size in a range from about 150 microns to about 300 microns, such as from about 150 microns to about 250 microns for the second particle size in bimodal size compositions, and a gelled inorganic binder, such as gelled colloidal silica. At least one gelling agent, such as at least one of hydrochloric acid, sulfuric acid, nitric acid, citric acid, and acetic acid, ammonium hydroxide, sodium hydroxide, and triethanol amine (hereinafter "TEA") may be added either before (e.g., as a pre-mix with the gelled inorganic binder) or during batching in order to gel the inorganic binder. Alternatively a non-gelled composition may be used. Such compositions can provide skins that set in a porous ceramic honeycomb body (and be thereby permanently sealed to the channel walls) at a temperature of less than 200° C., such as less than 100° C., and further such as less than 50° C., including about 25° C. Further non-limiting exemplary embodiments of cement compositions used for skinning are discussed below.

Skin compositions are described in U.S. Provisional Patent Application No. 61/602,883 and U.S. patent application Ser. No. 13/302,262, the contents of which are incorporated herein by reference in their entirety. According to exemplary embodiments the skin composition may be a single glass powder composition including a cement comprising a glass powder as a low thermal expansion filler material, a binder and a solvent or vehicle for carrying the solid constituents of the glass-based cement. The glass of the glass powder filler material may be an amorphous fused silica ($SiO_2$), ground cordierite, AT grog, or silica soot. The glass powder filler material can have a median particle size (D50) between 10 and 20 μm, with a minimum particle size between 7 μm and 75 μm and a maximum particle size between 50 μm and 70 μm. Particle size determined as a mass-based equivalent spherical diameter. The glass powder filler material may comprise, for example, from 60-80 wt. % of the total inorganic components of the cement. Suitable silica powder filler materials are available, for example, under the trade name Teco-Sil, available from CE Minerals of Tennessee Electro Minerals Incorporated, Tennessee, USA. All particle size measurements herein were made with a Microtrac Inc. particle size analyzer, unless otherwise indicated.

According to exemplary embodiments the skin composition may include an amorphous glass-based cement, the cement formed from a dual glass powder composition comprising a first (fine) glass powder as a low thermal expansion filler material, a second (coarse) glass powder as a low thermal expansion filler material, a binder and a solvent or vehicle for carrying the solid constituents of the glass-based cement. The glasses of both the first glass powder filler material and the second glass powder filler material may be amorphous fused silica having particle sizes greater than about 1 μm. The distribution of glass powder filler material particle size can be multimodal in that a distribution of the glass powder filler material with particle sizes greater than about 1 μm exhibits multiple modes (local maximums) of particle sizes. In one embodiment, the amorphous glass-based cement comprises a bimodal particle size distribution of amorphous glass particles with a particle size greater than about 1 μm. The glass based cement may include a first glass powder filler material wherein a median (D50) particle size of the first glass powder filler material can be in a range from about 10 to about 50 μm, from about 15 μm to about 50 μm, from about 20 μm to about 45 μm or from about 30 μm to about 45 μm, with a D10 in a range from about 1 μm to about 10 μm and D90 in a range from about 25 μm to about 125 μm. A median (D50) particle size of the second glass powder filler material can be in a range from about 150 μm to about 300 μm, in a range from about 150 μm to about 250 μm, in a range from about 170 μm to about 230 μm, in a range from about 180 μm to about 220 μm, with D10 in a range from about 100 μm to about 150 μm, and D90 in a range from about 250 μm to about 350 μm. Particle sizes are determined as a mass-based equivalent spherical diameter. As used herein, the term D50 represents the median of the distribution of particle sizes, D10 represents the particle size in microns for which 10% of the distribution are smaller than the particle size, and D90 represents the particle size in microns for which 90% of the distribution are smaller than the particle size. The dual glass based cement may contain, for example, an amount of the first glass powder filler material in a range from about 20 to about 60 wt. % of the total weight of the inorganic solid components of the cement, in a range from about 25 wt. % to about 50 wt. %, in a range from about 25 wt. % to about 40 wt. %, or in a range from about 25 wt. % to about 35 wt. %. The glass based cement may contain, for example, an amount of the second glass powder filler material in a range from about 10 wt. % to about 40 wt. % of the total weight of the inorganic solid components of the cement, in a range from about 15 wt. % to about 40 wt. %, in a range from about 20 wt. % to about 35 wt. %.

In one exemplary embodiment, D50 of the first glass powder filler material may be in a range from about 34 μm to about 40 μm, and a median particle size of the second glass powder filler material is in a range from about 190 μm to about 280 μm. In one example, the first glass powder filler material has a D10 of about 6.0 μm, a D50 of about 34.9 μm and a D90 of about 99 μm. In another example, the first glass powder filler material has a D10 of about 6.7 μm, a D50 of about 39.8 μm, and a D90 of about 110.9 μm. In still another example, the first glass powder has a D10 of about 2.7 μm, a D50 of about 13.8 μm and a D90 of about 37.8 μm, and as yet another example, the first glass powder filler material has a D10 of about 2.8 μm, a D50 of about 17.2 μm and a D90 of about 47.9 μm.

The ratio of the second glass powder filler material to the first glass powder filler material may be in a range from about 1:4 to about 1:1, such as about 1:3.5 to about 1:1, from about 1:3 to about 1:1, from about 1:2.5 to about 1:1, from about 1.2 to about 1:1 or from about 1:1.5 to about 1:1. In an exemplary embodiment, the ratio of the second glass powder filler material to the first glass powder filler material is 1:1.

To provide the cement compositions of the present disclosure, the inorganic powders comprising any of the above inorganic powders and any optional inorganic additive components can be mixed together with a suitable organic and/or inorganic binder material. The organic binder material may comprise one or more organic materials, such as a cellulose ether, methylcellulose, ethylcellulose, polyvinyl alcohol, polyethylene oxide and the like, or in some embodiments a gum-like material such as Actigum®, xanthan gum or latex. For example, A4 Methocel is a suitable organic binder. Methocel A4 is a water-soluble methyl cellulose polymer binder available from Dow Chemical. A suitable inorganic binder may comprise colloidal silica or alumina comprising nanometer-scale silica or alumina particles suspended in a suitable liquid, such as water. The inorganic binder material can be present in the cement composition in an amount less than about 10% of the total weight of inorganic solids present in the cement, and in some exemplary embodiments inorganic binders are present in an amount equal to or less than about 5 wt. %, and in certain other exemplary embodiments in a range from about 2 wt. % to about 4 wt. % taking into account the fluid portion of the organic binder (wherein the weight contribution of the fluid portion is removed). A suitable colloidal silica binder material is Ludox HS40 produced by W. R. Grace. Typical colloidal binder materials may comprise approximately 40% by weight solid material as a suspension in a deionized water vehicle.

In some exemplary embodiments, the single and dual glass powder cements described supra may also include an inorganic fibrous reinforcing material. For example, aluminosilicate fibers may be added to the cement mixture to strengthen the honeycomb structure after application of the skin. For example, the cement may include an inorganic fibrous material from about 25 to about 50 wt. % of the total weight of the inorganic solid components of the cement, from about 30 to about 50 wt. %, and in some embodiments from about 35 to about 45 wt. % of the total weight of the inorganic solid components of the cement. In certain other embodiments, fibrous inorganic reinforcing materials may be present in an amount from about 36 wt. % to about 43 wt. % as a percentage of the total weight of the inorganic solids of the cement composition. A suitable inorganic fibrous reinforcing material is Fiberfrax QF 180, available from Unifrax, however, any high aspect ratio refractory particulate could be used.

Typically, the liquid vehicle or solvent for providing a flowable or paste-like consistency has included water, such as deionized (DI) water, although other materials may be used. The liquid vehicle content may be present as a super addition in an amount equal to or less than about 30 wt. % of the inorganic components of the cement mixture, can be in a range from about 10 wt. % to about 25 wt. % of the inorganic components of the cement mixture. However, the liquid vehicle is typically adjusted to obtain a viscosity suitable to make the cement easy to apply.

In some embodiments the cement may optionally further contain organic modifiers, such as adhesion promoters for enhancing adhesion between the cement and the honeycomb body. For example, Michem 4983 has been found suitable for this purpose.

In certain exemplary embodiments, the cement mixture sets at a temperature of less than 1000° C., such as a temperature of less than 800° C., and further such as a temperature of less than 600° C., and yet further such as a temperature of less than 400° C., and still yet further such as a temperature of less than 200° C. In certain exemplary embodiments, the cement mixture is capable of setting at room temperature (i.e., at about 23° C.).

Cement compositions described herein can exhibit viscosities well suited for forming an external skin over a honeycomb core. For example, compositions according to the embodiments herein can have an infinite shear viscosity equal to or less than about 12 Pascal-seconds (Pa·s), equal to or less than about 5 Pa·s, or equal to or less than about 4 Pa·s. For a shear rate of 10 $s^{-1}$, the shear viscosity may, for example, be equal to or less than about 400 Pa·s, equal to or less than about 350 Pa·s or less than or equal to about 300 Pa·s. Viscosity was measured using a parallel plate viscometer.

Calcining of cement compositions disclosed herein can be conducted in a box furnace with a linear ramp to 600° C. in 3 hours, followed by a hold for 3 hours at 600° C., then followed by a ramp down to room temperature over a time period of 3 hours. In commercial use, the ceramic article can be wash coated with catalyst followed by a heat treatment to remove organic materials. The ceramic article can also be canned with a mat material that may also require heat treatment to remove organic materials. The calcining process simulates service conditions experienced by the ceramic article.

The composition of the skin cement is not particularly limited and can include, for example, a skin cement of single glass powder compositions, dual glass powder compositions, single glass powder with fibrous reinforcing material compositions, dual glass powder with fibrous reinforcing material compositions, inorganic filler and crystalline inorganic fibrous material compositions, and dual glass powder and crystalline inorganic fibrous material compositions.

The inline inspection and control unit 140 can include an inspection unit 144 to inspect skin 136 surface quality. The inspection unit 144 can include a laser unit 148 to emit a light beam 150 and a detection unit 152 such as a charged coupled device (CCD) camera to detect the light beam 150 scattered from the skin 136. The inspection unit 144 provides a signal 168 based on the detected light beam 150 scattered from the skin 136 surface. The inline inspection and control unit 140 can include a control unit 160 to receive the signal 168 in a receiver module 164, analyze the signal 168 in a signal analyzer module 172, and a transmitter module 176 to transmit a control signal 180 to a process controller 184 to control a process of the skinning system 116 in response to the analysis.

The control unit 160 may be embodied directly in hardware, in a software module executed by a processor, or in a combination of the two to implement the methods or algorithms described in connection with the embodiments disclosed herein. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of non-transitory storage medium known in the art. An exemplary storage medium is coupled to a processor of the control unit 160 such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

While the control unit 160 has been described as separate from the inspection unit 144, this disclosure is not so limited, that is, the control unit 160 or any of the modules 164, 172, 176 thereof may constitute the inspection unit 144. Further, any unit or module of the in line inspection and control unit 140 may be integral with any other unit or module thereof. For example, the control unit 160 may be integral with the detection unit 152, and the receiver module 164, the signal analyzer module 172, and the transmitter module 176 may be one integral module. Also, well-known structures, materials, or operations are not shown or described in detail to avoid obscuring aspects of the disclosed subject matter. For example, the control unit 160 may include a storage device, a processing unit, power supply, and the like, and signals 168, 180 may be transmitted wirelessly, over cables, optical fiber, and the like.

As the skinned part 122 exits the unipipe 114 in the axial skinning direction 124 it passes through the light beam 150 emitted from the laser 148. The light beam 150 illuminates a line on the periphery of the part 122 perpendicular to the skinning direction 124. As the skinned part 122 passes through the light beam 150 emitted from the laser 148 it is inspected by the inspection unit 144. The inspection unit may include a plurality of lasers 148 and detection units 152. Accordingly, real-time inspection of parts 122 comprising wet skins 136 can be inspected as they exit the skinning unipipe 114 in these exemplary embodiments of the disclosure.

While described as the skinned part 122 passing through the light beam 150 in these exemplary embodiments, this disclosure is not so limited. That is, the skinned part 122 may be stationary and the inspection unit 144 may move axially past the skinned part 122.

Figure 2:
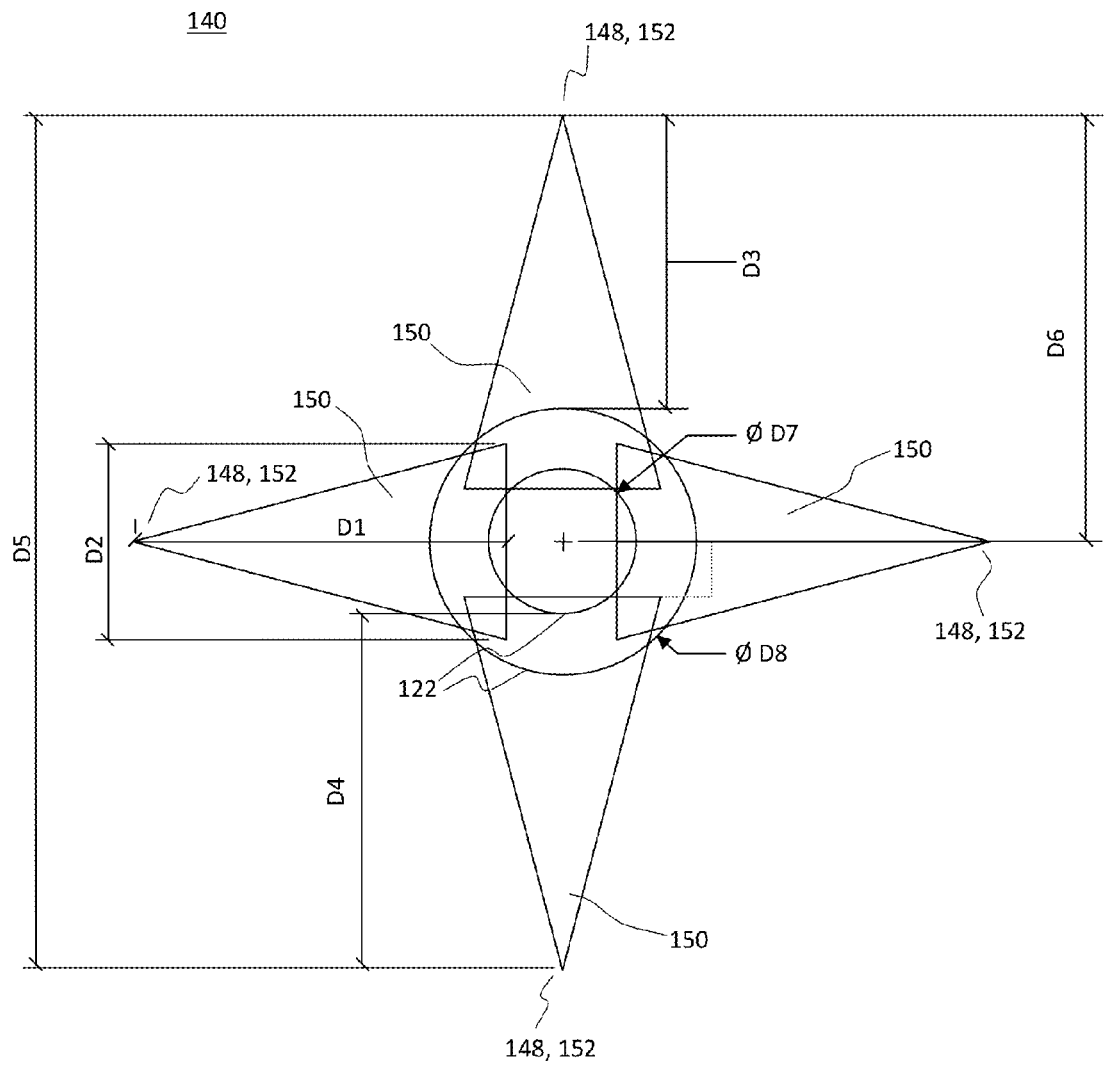
FIG. 2 shows a schematic top view of a projection of four line lasers located 90 degrees apart to cover an outer surface cross section perpendicular to a longitudinal axis of a skinned honeycomb body according to exemplary embodiments of the disclosure.

FIG. 2 shows a schematic top view of a projection of four line lasers 148 and detection units 152 located 90 degrees apart to cover an outer surface cross section perpendicular to a longitudinal axis of a skinned honeycomb body 122 according to exemplary embodiments of the disclosure. The maximum and minimum part 122 diameters for the line laser unit 148 and detection unit 152 arrangement illustrated in FIG. 2 are indicated by Ø D8 and Ø D7, respectively. In an exemplary embodiment, D1 may be about 17.7 in (45 cm), D2 may be about 9.45 in (24 cm), D3 may be about 13.8 in (35 cm), D4 may be about 16.8 in (42.7 cm), D5 may be about 40.6 in (103 cm), D6 may be about 20.3 in (51.6 cm), D7 may be about 7 in (17.8 cm), and D8 may be about 13 in (33 cm). The arrangement of line laser units 148 and detection units 152 including number thereof, depends on size and shape of the part 122 periphery and desired circumferential resolution. In exemplary embodiments the circumferential resolution is sufficient to detect 1 mm wide skin defects, for example, the circumferential resolution may be sufficient to detect 700 μm wide skin defects, 500 μm wide defects, 100 μm wide defects, 50 μm wide defects, or even 10 μm wide defects, where the width of the defect is in the circumferential direction, that is, the direction perpendicular to the axial direction regardless of the part 122 shape.

Figure 3:
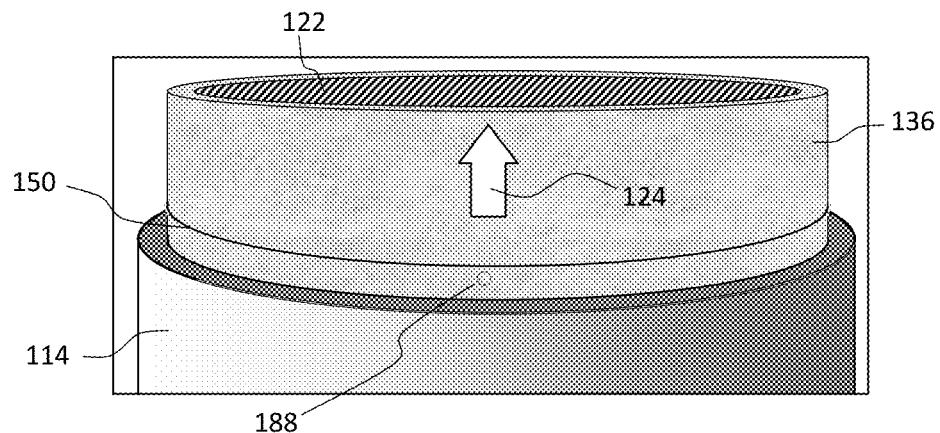
FIG. 3 shows a perspective side view of a honeycomb structure comprising a skin being axially applied in a unipipe and passing through an inspection laser line as the honeycomb body exits the unipipe according to these exemplary embodiments of the disclosure.

FIG. 3 shows a perspective side view of a skinned honeycomb structure 122 comprising a skin 136 being axially applied in a unipipe 114 and passing through an inspection laser line 150 as the honeycomb body 122 exits the unipipe 114 according to these exemplary embodiments of the disclosure. The part lifting unit 132 is not shown for convenience. At the bottom center of the skinned part 122 is a pock 188 or small depression in the skin surface that was generated during the skinning process and is about to pass through the laser light beam 150. A pock 188 is a crater defect in the skin 136. As used herein, a pit is a pock 188 that penetrates the thickness of the skin 136 from the skin surface to the honeycomb structure 100 beneath the skin 136.

Figure 4:
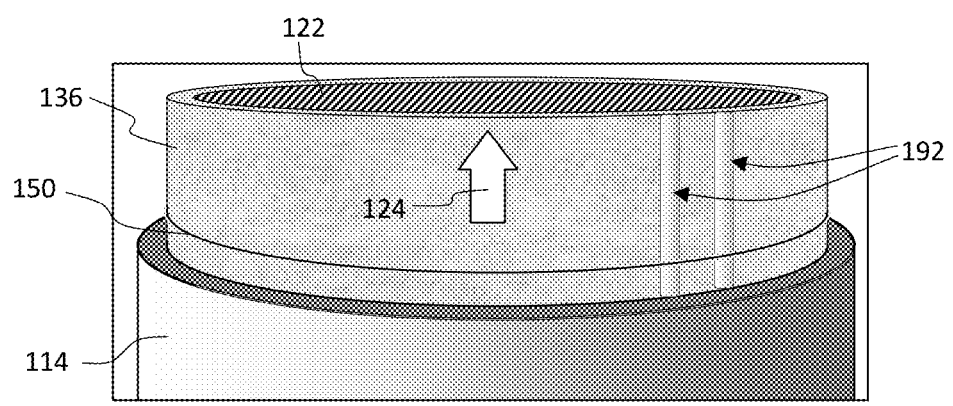
FIG. 4 shows a perspective side view of a honeycomb structure comprising a skin being axially applied in a unipipe and passing through an inspection laser line as the honeycomb body exits the unipipe according to these exemplary embodiments of the disclosure.

FIG. 4 shows a perspective side view of a honeycomb structure 122 comprising a skin 136 being axially applied in a unipipe 114 and passing through an inspection laser line 150 as the honeycomb body 122 exits the unipipe 114 according to these exemplary embodiments of the disclosure. On the right side of the part 122 are two areas where excessive localized pressure or reduced viscosity has produced extra skin cement 118 causing the cement to bulge out from the skin 136 surface referred to herein as "fast flow" defect 192. When there is a lack of skin cement 118 on a portion of the honeycomb body 122 this is referred to herein as "starvation" defect. That is, a starvation defect can be understood as the opposite of a fast flow defect 192.

Figure 5:
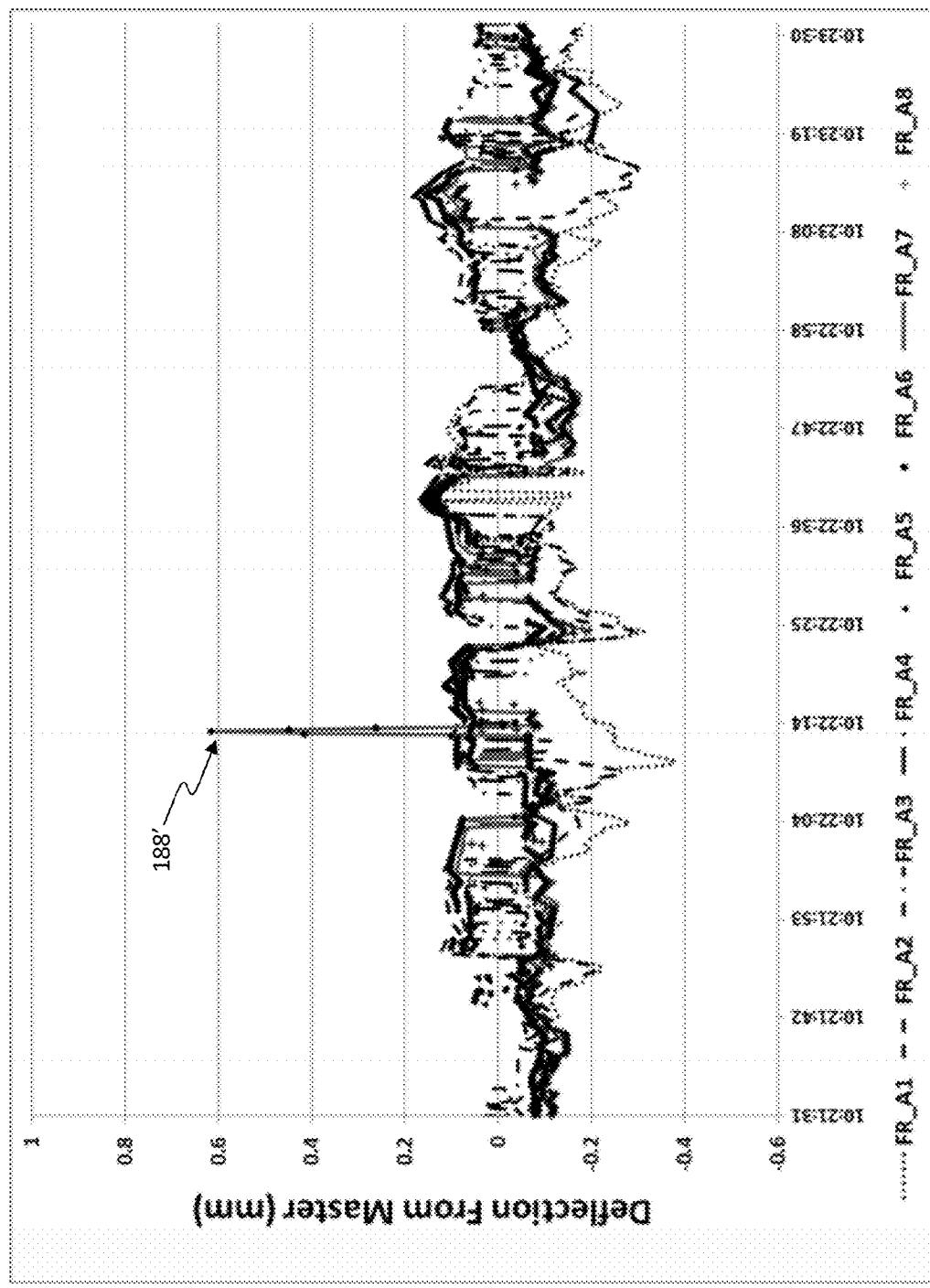
FIG. 5 presents data output of laser detectors in an Example embodiment illustrating detection of a pock according to exemplary embodiments of the disclosure.

FIG. 5 presents data output of laser detection units 152 in an Example embodiment illustrating detection of a pock 188 according to exemplary embodiments of the disclosure. In the Example shown in FIG. 5, four line lasers 148 and detectors 152 were arranged around the part 122 exiting the unipipe 114 as depicted in FIGS. 1 and 2, as described herein. The field of view of each of the four line lasers 148 was divided into eight sections (areas). During a calibration, a master profile was stored in a memory representing a defect-free part. The master profile comprises a measurement signal from the detected laser of a defect-free part. At specified time intervals or on a continuous basis during the part skinning as the part 122 passes through the inspection laser line 150, each detected inspection laser line generated an instant measurement signal (real-time data). The instant measurement signal was compared to the master profile. The difference between the master profile and the instant measurement signal for all eight areas of all four lasers 148 was analyzed to find anomalies that indicate defects. The pock 188 defect seen in FIG. 3 shows up as a positive spike 188' in the time series data in FIG. 5. Depressions in the skin surface are shown as positive deviations in the data while bulges are shown as negative deviations as shown in FIG. 6, which displays data detecting a fast flow defect.

Figure 6:
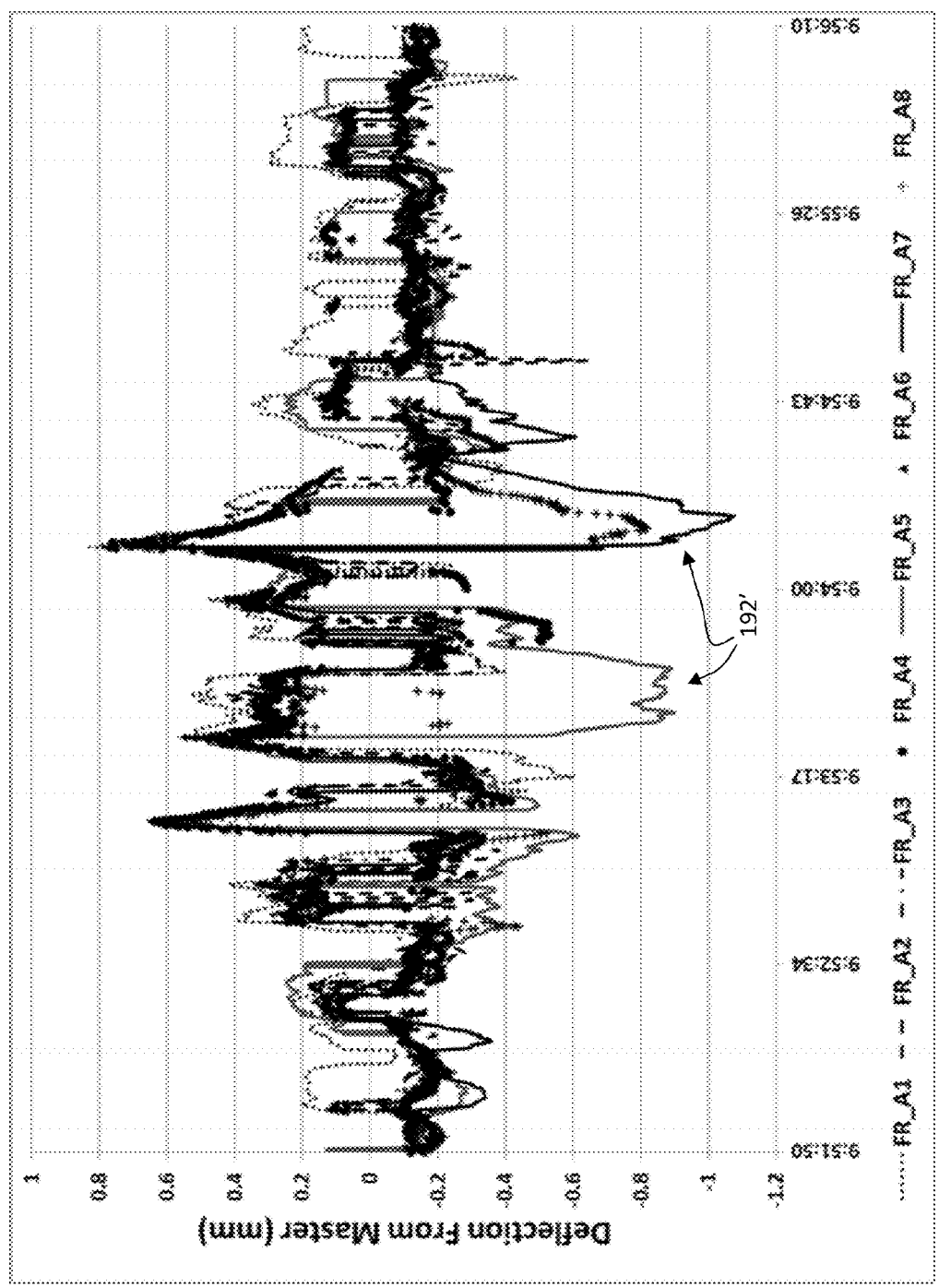
FIG. 6 presents data output of laser detectors in an Example embodiment illustrating detection of two skin cement bulges (fast flow) according to exemplary embodiments of the disclosure.

FIG. 6 presents data output of the laser detectors 152 in the Example embodiment illustrating detection of a fast flow defect 192 according to these exemplary embodiments of the disclosure. In the Example shown in FIG. 6, four line lasers 148 and detectors 152 were arranged around the part 122 exiting the unipipe 114 as depicted in FIGS. 1 and 2, and as described above with reference to FIG. 5. The difference between the master profile and the instant measurement signal for all eight areas of all four lasers 148 was analyzed to find anomalies that indicate defects. The fast flow defect 192 seen in FIG. 4 comprises bulges of excess cement material in the applied skin and shows up as negative spikes 192' (dips) in the time series data in FIG. 6. The fast flow bulges 192 are shown as negative deviations 192' in FIG. 6 and are wider peaks 192' in the data than the pit or pock peak 188'. Fast flow appears as wider peaks 192' because they tend to last longer in time, for example, the length of a part, and are not localized defects such as pocks.

Figure 7:
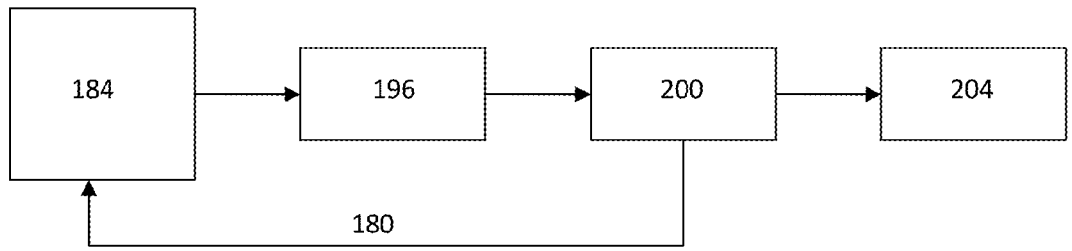
FIG. 7 shows a schematic control architecture in which skin inspection signal measurement can be utilized in a feedback control scheme to adjust skinning process parameters to reduce or eliminate anomalies, defects, non-uniformities, and the like according to exemplary embodiments of the disclosure.

FIG. 7 shows a schematic control architecture 700 in which skin inspection signal measurement can be utilized in a feedback control scheme to adjust skinning process parameters to reduce or eliminate anomalies, defects, non-uniformities, and the like according to exemplary embodiments of the disclosure. In FIG. 7 a skinning process controller 184 provides skinning process parameters to the skinning apparatus 116. Skinning process parameters include such parameters as cement pressure in the manifold 120 and unipipe 114, the part feed rate through the unipipe 114, for example, by controlling part handling unit 110 and part lifting unit 132 speeds, the skinning cement 118 chemistry fed into the manifold 120 and unipipe 114, and disposed on the honeycomb core 128, for example, amount of water in the cement, amount of air in the cement, or density of the cement skin batch, and the like.

At skinning process 196 the skinning apparatus 116 applies the process parameters from 184 to skin the honeycomb structure 100. A skin quality measurement 200 is conducted as the skinned honeycomb body 122 exits the unipipe 114 and passes through inspection unit 144 of the inline inspection and control unit 144, to inspect skin surface quality as described with reference to FIGS. 1-6. The skinned part 122 emerges at output 204. When a defect is detected and identified in the skin quality measurement 200 a control signal 180 provides feedback to the process controller 184 to control a process of the skinning system 100 in response to the skin quality measurement 200. The feedback to the process controller 184 to control a process of the skinning system 116 in response to the skin quality measurement 200 reduces or eliminates defects in subsequently skinned parts 122.

Figure 8:
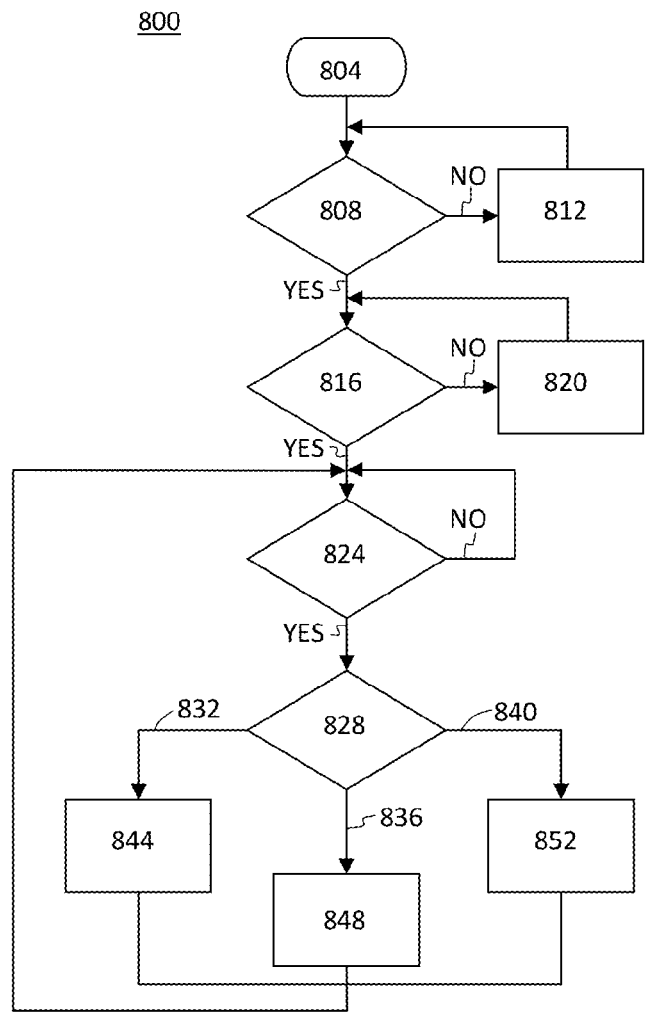
FIG. 8 is a process diagram illustrating a method of utilizing data from a honeycomb body skin inspection unit to control skinning process parameters to reduce or eliminate anomalies, defects, non-uniformities, and the like in the honeycomb body skinning process according to exemplary embodiments of the disclosure.

FIG. 8 is a process diagram illustrating a method of utilizing data from a honeycomb body skin inspection unit to control skinning process parameters to reduce or eliminate anomalies, defects, non-uniformities, and the like in the honeycomb body skinning process according to exemplary embodiments of the disclosure. The method can use the axial skinning system 116 having the inline skin quality inspection and control unit 140 according to the exemplary embodiments of the disclosure described with reference to FIGS. 1-7. In FIG. 8, operation 804 indicates start of the method. In operation 808 the "on" or "off" state of the inline skin quality inspection and control unit 140 is determined. When the inspection and control unit 140 is in the "off" state operation 812 turns the inspection and control unit 140 to the "on" state. When the inspection and control unit 140 is in the "on" state operation 816 determines whether data from the detection unit 152 has been received by the controller 160 and analyzed by the signal analyzer 172.

When the data from the detection unit 152 has not been received and analyzed, operation 820 provides a stand-by state where the inspection and control unit 140 returns to operation 816. Operation 820 may provide a time period, zero-mean sensor data, and the like before returning the inspection and control unit 140 to operation 816. When the data from the detection unit 152 has been received and analyzed, operation 824 determines whether a skin defect has been detected in response to the analysis by the signal analyzer 172.

When a skin defect has been detected in operation 824, operation 828 determines which type of defect is detected. When the type of defect detected in operation 828 is a fast flow or starvation 832, operation 844 applies the system process control rules related to fast flow and starvation defect type. The process controller 184 applies the system process control rules to control a process of the skinning system 116 in response to the analysis.

According to exemplary embodiments of the disclosure, example system process control rules are shown in Table 1. In these exemplary embodiments, the part conveying unit 110, 132 may be configured to convey the part 100, 122, 128 at axial speeds of about 1 to 100 mm/s. The skinning pressure may be in a range of about 1 psi ($6.89 \times 10^3$ Pa) to about 6 psi ($4.14 \times 10^4$ Pa) where the manifold meets the unipipe. A peak deflection from master signal between about −0.6 mm and about −0.8 mm may correspond to a deviation from average skin surface by about 0.6 mm to about 0.8 mm. The average skin surface indicates the topology of a defect free surface. For clarity, when a deflection of less than about −0.8 mm is used herein, the absolute value of the deflection ($|\Delta x|$, where $\Delta x$ is the deflection) is greater than about 0.8 mm. Likewise, when a deflection of greater than about +0.8 mm is used herein, the absolute value of the deflection ($|\Delta x|$) is greater than about 0.8 mm.

TABLE 1

| Condition | Control Action |
|---|---|
| If 5 consecutive parts have fast flow skin defect with peak deflection from master signal between about −0.6 mm and about −0.8 mm | Decrease skinning pressure set point by about 1 psi ($6.89 \times 10^3$ Pa) and proceed with skinning for about 2 minutes before the next process parameter adjustment is made |
| If 2 consecutive parts have fast flow skin defect with peak | Decrease skinning pressure set point by about 2 psi ($1.38 \times 10^4$ Pa) and |

TABLE 1-continued

| Condition | Control Action |
|---|---|
| deflection from master signal less than about −0.8 mm | proceed for about 2 minutes before the next process parameter adjustment is made |
| If 5 consecutive parts have starvation skin defect with peak deflection from master signal between about +0.6 mm and about +0.8 mm | Increase skinning pressure set point by about 1 psi (6.89 × 10³ Pa) and proceed for about 2 minutes before the next process parameter adjustment is made |
| If 2 consecutive parts have starvation skin defect with peak deflection from master signal greater than about +0.8 mm | Increase skinning pressure set point by about 2 psi (1.38 × 10⁴ Pa) and proceed for about 2 minutes before the next process parameter adjustment is made |

When the type of defect detected in operation 828 are lines or drag marks on the skin 836, operation 848 raises a flag to check the part handling unit 110 to part lifting unit 132 top/bottom "handshake" or integrity of the unipipe 114. An operator may be alerted by the flag in operation 848 to perform the check. That is, a line around the part 122 in a direction perpendicular to the axial direction may indicate a mismatch in alignment between the part handling unit 110 and the part lifting unit 132 alerting an operator to perform alignment of the part handling unit 110 and the part lifting unit 132. A drag mark may indicate debris in the unipipe 114 alerting an operator to perform cleaning of the unipipe 114. When the type of defect detected in operation 828 are lines or drag marks on the skin 836, the process controller 184 may shut down the axial skinning apparatus 116 in an alternative exemplary embodiment.

When the type of defect detected in operation 828 is a pit/pock 840 operation 852 applies the system process control rules related to pits and pocks defect type. The process controller 184 applies the system process control rules to control a process of the skinning system 100 in response to the analysis. Example system process control rules for pits and pocks are shown in Table 2

TABLE 2

| Condition | Control Action |
|---|---|
| If 10 consecutive parts have a number of pits and pocks occurrence above a threshold | Increase skin cement batch density by 0.1 units and proceed with skinning for 30 minutes before next adjustment is made |
| If 5 consecutive parts have a number of pits and pocks occurrence above 3X the threshold | Increase skin cement batch density by 0.2 units and proceed with skinning for 30 minutes before next adjustment is made |

Accordingly, these exemplary embodiments of the disclosure involve hardware and control algorithms to determine the location and size of micron- to millimeter-size defects introduced during an axial skinning process as well as the control algorithm to minimize or eliminate these defects in an automated fashion. The defect detection process can begin with projecting line lasers 148 onto the outside surface of a part 122 where the laser lines 150 are perpendicular to the axis of motion 112 of the axial skinner 116. The lasers 148 can be situated at the exit of the skinning unipipe 114 where the part has had skin applied. The laser lines 150 can be measured by a camera 152 and optical filter using triangulation to detect any curvature or defects in the skin surface (laser profilometer). For example, large aspect ratio laser line scanners may be selected and combined such that four are disposed at 90 degree increments to produce complete or nearly complete coverage of the outside of a largest part 122. Complete coverage of the largest part 122 may be accomplished with an additional scanner 148, 152 if necessary.

The scan rate of the laser profilometer may be greater than about 1 kHz and thus nearly continuous measurement of the outside surface of the skinned parts is possible in these exemplary embodiments where skin speeds may be in the 5-10 mm/s range. The laser profilometers may be rigidly mounted at a distance needed to cover a range of products of interest, for example about 7 inch (17.78 cm) to about 13 inch (33.02 cm) diameter round cylindrical parts. After the lasers 148 are mounted an ideal surface shape can be captured, one that would indicate a perfect part (defect-free). This profile can be captured and stored in a storage device as the master profile and used to compare against each successive measured profile. Each real-time measurement of the skinned part 122 has the master profile subtracted from it and then the length of each laser line is divided into eight sections. Combining the data from four lasers produces 32 such sections covering the entire part. The analyzer 172 then searches across each of these subsections and calculates the largest deviation in the radial direction from the current measurement and the master profile and reports this value at the sampling rate of the system, for example, at 1 kHz. Thus 32 measurements representing the maximum radial defect measurement around the skinned part can be reported to the controller 160 to be stored in a data archive system and used for active (real-time) control of the skinning process.

The analyzer 172 can be configured to receive the signal from the profilometer at greater than or equal to a frequency while the part conveying unit 110, 132 can be configured to convey the part 122 at an axial speed such that successive scans and transmissions are spaced apart by no more than 1 mm in the axial direction. For example, the laser profilometer can be configured to scan the illuminated line 150 and transmit the signal 168 to the controller 160 at greater than or equal to a frequency and the part conveying unit 110, 132 can be configured to convey the part 122 at an axial speed such that successive scans and transmissions are spaced apart by about 1 mm to about 50 μm in the axial direction 112. For example, the frequency can be in a range between about 20 Hz and about 2 kHz and the part conveying unit 110, 132 can convey the part at an axial speed in a range between 2 mm/s and 100 mm/s. In these exemplary embodiments the axial resolution is sufficient to detect 1 mm long skin defects, for example, the axial resolution may be sufficient to detect 700 μm long skin defects, 500 μm long defects, 100 μm long defects, 50 μm long defects, or even 10 μm long defects, where the length of the defect is in the axial direction.

The controls architecture for the axial skinning process can respond to a quality metric to adjust critical system parameters like manifold pressure, skin speed, and skin cement batch chemistry. The inspection method according to these exemplary embodiments allows the skin process controller 184 to make adjustments to these parameters to maintain good skin quality or reduce length of upsets thereby reducing waste and cost in the process.

Statistical process control (SPC) principles can be applied to reduce defects and maintain good skin quality according to these exemplary embodiments of the disclosure. Each family of skin defects can be managed separately as the root cause of the defects may be different. Depending on the type of skin defects occurring, a particular control strategy path can be chosen. The controlled process parameter (control knob) to affect a particular skin defect may also be different. For example, if "fast flow" or "starvation" type of skin defect is occurring, then the control knob can be the skinning pressure alone, the skinning velocity alone, or a combination of skinning pressure and skinning velocity. Herein, skinning velocity refers to the velocity of the part 100, 122, 128 through the unipipe 114. Similarly, if "pocks" and "pits" are being formed on the skin, then the control knob in this case can be the skin cement batch composition, such as skin cement batch density.

This control method according to exemplary embodiments can be implemented either in a semi-automatic manner or in a fully automatic mode. In the semi-automatic mode, the controller 160 can use the data from the skin inspection system 144 and compute the desired control move to be made and display the move in the control room where the operator can decide whether to make the suggested move or not. In the fully automatic mode, the controller 160 can make the moves automatically.

Once the skin material 118 has been applied to the honeycomb structure 128 in a manner as described herein, the skin 136 can be optionally dried and/or fired. The optional drying step can comprise first heating the skin 136 in a humidity controlled atmosphere at a temperature and for a period of time sufficient to at least substantially remove any liquid vehicle that may be present in the skin material. As used herein, at least substantially removing any liquid vehicle includes the removal of at least 95%, at least 98%, at least 99%, or even at least 99.9% of the liquid vehicle present in the skin 136 prior to firing. Further, the heating can be provided by any conventionally known method, including for example, hot air drying, RF and/or microwave drying in a humidity controlled atmosphere.

The optional firing step can include conditions suitable for converting the skin material to a primary crystalline phase ceramic composition include heating the honeycomb with applied skin material 122 to a peak temperature of greater than 800° C., 900° C., and even greater than 1000° C. A ramp rate of about 120° C./hr during heating may be used, followed by a hold at the peak temperature for a temperature of about 3 hours, followed by cooling at about 240° C./hr.

Some of the functional units described in this specification have been labeled as modules, controllers, and units in order to emphasize their implementation independence. For example, a module, controller or unit, herein after "module," may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like. A module may also be implemented with valves, pistons, gears, connecting members, and springs, or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

Reference throughout this specification to exemplary embodiments and similar language throughout this specification may, but do not necessarily, refer to the same embodiment. Furthermore, the described features, structures, or characteristics of the subject matter described herein with reference to an exemplary embodiment may be combined in any suitable manner in one or more exemplary embodiments. In the description, numerous specific details are provided, such as examples of controls, structures, algorithms, programming, software modules, user selections, network transactions, database queries, database structures, hardware modules, hardware circuits, hardware chips, etc., to provide a thorough understanding of embodiments of the subject matter. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the disclosed subject matter.

The schematic flow chart diagrams and method schematic diagrams described above are generally set forth as logical flow chart diagrams. As such, the depicted order and labeled steps are indicative of representative embodiments. Other steps and methods may be conceived that are equivalent in function, logic, or effect to one or more steps, or portions thereof, of the methods illustrated in the schematic diagrams. Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown.

It will be apparent to those skilled in the art that various modifications and variations can be made in the present disclosure without departing from the spirit or scope of the disclosure. Thus, it is intended that the appended claims cover the modifications and variations of this disclosure provided they come within the scope of the appended claims and their equivalents.

The invention claimed is:

1. An in situ inspection system to inspect a honeycomb body skin in a honeycomb body skinning system for at least one defect, the inspection system comprising:
    a part conveying unit that moves a honeycomb body comprising the skin disposed thereon in an axial direction;
    an inspection unit, comprising:
        a line illuminator configured to generate a line illumination on the skin perpendicular to the axial direction, and
        a detector configured to detect the line illumination scattered from the skin and generate a signal based on the detected line illumination;
    a controller configured to receive the signal generated by the detector, compare the received signal to a previously stored defect free signal in real-time, and control at least one skinning process parameter based on the comparison,
    wherein the controller is configured to control the skin cement batch density in response to the defect identified as at least one of a pit and a pock, and the controller is configured to control at least one of the skin cement pressure and a velocity of the part conveying unit in response to the defect identified as a starvation.

2. The inspection system of claim 1, wherein the comparison is configured to identify a difference between the previously stored defect free signal and the received signal at least one of greater than a positive threshold and less than a negative threshold as a defect.

3. The inspection system of claim 2, wherein the comparison is configured to identify the difference greater than the positive threshold as the defect of not enough skin on the honeycomb body.

4. The inspection system of claim 3, wherein the comparison is configured to identify the defect as at least one of a pit, pock, and a starvation.

5. The inspection system of claim 1, wherein the controller is configured to control skin process parameters to not change for a stabilizing time period after controlling at least one skinning process parameter to change based on the comparison.

6. The inspection system of claim 4, wherein the comparison is configured to measure time that the difference is greater than the positive threshold to determine whether pit and pock or starvation.

7. The inspection system of claim 2, wherein the comparison is configured to identify the difference less than the negative threshold as a defect of too much skin on the honeycomb body.

8. The inspection system of claim 7, wherein the comparison is configured to identify the defect as a fast flow and the controller is configured to control the skin cement pressure in response to the defect identified as fast flow.

9. The inspection system of claim 8, wherein the controller is configured to control skin process parameters to not change for a stabilizing time period after controlling at least one skinning process parameter to change based on the comparison.

10. The inspection system of claim 8, wherein the comparison is configured to measure time that the difference is less than the negative threshold to determine the defect is fast flow.

11. The inspection system of claim 1, wherein the line illuminator comprises a laser and the detector comprises a laser profilometer comprising a charged coupled detector (CCD) camera and an optical filter.

12. The inspection system of claim 11, wherein the laser profilometer is configured to scan the illuminated line and transmit the signal to the controller at greater than or equal to a frequency and the part conveying unit is configured to convey the part at an axial speed such that successive scans and transmissions are spaced apart by no more than 1 mm in the axial direction.

13. The inspection system of claim 11, wherein the laser profilometer is configured to scan the illuminated line and transmit the signal to the controller at greater than or equal to a frequency and the part conveying unit is configured to convey the part at an axial speed such that successive scans and transmissions are spaced apart by about 1 mm to about 50 µm in the axial direction.

14. The inspection system of claim 13, wherein the frequency is in a range between about 20 Hz and about 2 kHz and the part conveying unit is configured to convey the part at an axial speed in a range between 2 mm/s and 100 mm/s.

15. The inspection system of claim 1, wherein the inspection unit is configured to begin inspection while the honeycomb body is in a unipipe of an axial skinning system and at least a portion of the honeycomb body has exited the unipipe.

16. The inspection system of claim 1, wherein the inspection unit comprises a plurality of line illuminators and detectors, and the controller is further configured to receive a plurality of signals from the plurality of detectors.

17. The inspection system of claim 16, wherein the inspection unit comprises the plurality of illuminators spaced evenly around the part conveying unit in a plane perpendicular to the axial direction and the plurality of detectors spaced evenly around the part conveying unit at least one of above and below the plane perpendicular to the axial direction such that the spatial resolution in a direction perpendicular to the axial direction of each detector is less than 500 µm on the skin surface, and the controller is configured to receive a plurality of signals from the detectors corresponding to a portion of the skin illuminated by the respective detected line illumination.

18. A method of manufacturing skinned honeycomb bodies, comprising:
conveying a honeycomb body comprising a skin disposed thereon in an axial direction;
in situ inspecting the skin comprising:
illuminating a line of the skin perpendicular to the axial direction, detecting the illuminated line scattered from the skin, and generating a signal based on the detecting;
comparing the signal to a previously stored defect free signal in real-time;
controlling at least one skinning process parameter based on the comparing;
controlling the skin cement batch density in response to the defect identified as at least one of a pit and a pock, and
controlling at least one of the skin cement pressure and a velocity of the part conveying unit in response to the defect identified as a starvation.

19. The method of claim 18, wherein comparing identifies a difference between the previously stored defect free signal and the received signal as at least one of greater than a positive threshold and less than a negative threshold as a defect.

20. The method of claim 18, wherein the laser detecting detects the illuminated line and generating generates the signal at greater than or equal to a frequency and the conveying conveys the honeycomb body at an axial speed such that successive detections and generations are spaced apart by no more than 1 mm in the axial direction.

21. The method of claim 18, wherein the laser detecting detects the illuminated line and generating generates the signal at greater than or equal to a frequency and the conveying conveys the honeycomb body at an axial speed such that successive detections and generations are spaced apart by about 1 mm to about 50 µm in the axial direction.

22. The method of claim 18, wherein
the illuminating a line of the skin perpendicular to the axial direction comprises illuminating a plurality of co-planar lines on adjacent segments of the skin,
the detecting comprises detecting the plurality of illuminated co-planar lines scattered from the skin,
generating the signal comprises generating a plurality of signals corresponding to each respective detected co-planar line,
comparing the signal comprises comparing each of the plurality of signals to a previously stored defect free signal at the corresponding segment in real-time, and
controlling at least one skinning process parameter based on the comparing.

* * * * *